United States Patent
Buan et al.

(10) Patent No.: US 6,532,958 B1
(45) Date of Patent: *Mar. 18, 2003

(54) AUTOMATED CONTROL AND CONSERVATION OF SUPPLEMENTAL RESPIRATORY OXYGEN

(75) Inventors: John S. Buan, Maple Grove, MN (US); Matthew F. Schmidt, Lino Lakes, MN (US); Catherine A. Nordman, St. Paul, MN (US)

(73) Assignee: Minnesota Innovative Technologies & Instruments Corporation, Lino Lakes, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/900,686

(22) Filed: Jul. 25, 1997

(51) Int. Cl.⁷ ................................................. A61M 16/00
(52) U.S. Cl. ........................... 128/204.23; 128/204.21; 128/898; 600/323
(58) Field of Search .......................... 128/204.14, 633, 128/664, 204.18–204.23, 204.26, 205.11, 205.23, 205.24, 207.14, 207.18, 203.12, 203.22, 200.24, 898; 600/322–341, 484

(56) References Cited

U.S. PATENT DOCUMENTS

| | | | |
|---|---|---|---|
| 2,414,747 A | 1/1947 | Kirschbaum | 128/142 |
| 2,912,979 A | 11/1959 | Lieber | 128/203 |
| 3,400,712 A | 9/1968 | Finan | |
| 3,400,713 A | 9/1968 | Finan | 128/203 |
| 3,493,703 A | 2/1970 | Finan | 200/153 |
| 3,734,091 A | 5/1973 | Taplin | 128/142 |
| 4,054,133 A | 10/1977 | Myers | 128/142.2 |
| 4,278,110 A | 7/1981 | Price et al. | 137/805 |
| 4,326,513 A | 4/1982 | Schulz et al. | 128/203.14 |
| 4,381,002 A | 4/1983 | Mon | 128/204.24 |
| 4,457,303 A | 7/1984 | Durkan | 128/204.24 |
| 4,461,293 A | 7/1984 | Chen | 128/204.23 |

(List continued on next page.)

FOREIGN PATENT DOCUMENTS

DE 4309923 A1 9/1994

OTHER PUBLICATIONS

D. Auerbach et al., "A New Oxygen Cannula System Using Intermittent–Demand Nasal Flow", *Chest*, 74, pp. 39–43 (1978).

N. Azhar et al., Automotic Feedback Control of Oxygen Therapy Using Pulse Oximetry, *Annual International Conference of the IEEE Engineering in Medicine and Biology Society*, 13 pp. 1614–1615 (1991).

I.R. Beddis, et al., "New Technique for Servo–Control of Arterial Oxygen Tension in Preterm Infants", *Archives of Disease in Childhood*, 54, pp. 278–280 (1979).

(List continued on next page.)

*Primary Examiner*—Glenn K. Dawson
(74) *Attorney, Agent, or Firm*—Mueting, Raasch & Gebhardt, P.A.

(57) ABSTRACT

Methods and systems for supplying supplemental oxygen to patients for use in sub-acute care which maintains healthy blood oxygen content in the patients by controlled dosing of oxygen with a measured response to the patient's actual blood oxygen content are disclosed. The dosing can be provided by simple ON/OFF control over the delivery of oxygen or the amount of oxygen delivered to the patient with each inhalation can be varied in response to the patient's need as determined by a more sophisticated control scheme, such as a PID loop control algorithm, that utilizes the difference between the patient's actual blood oxygen content and a target blood oxygen content and/or trends in the blood oxygen content. The systems and methods are particularly directed at patients receiving supplemental oxygen in a sub-acute care environment.

9 Claims, 4 Drawing Sheets

U.S. PATENT DOCUMENTS

| | | | |
|---|---|---|---|
| 4,462,398 A | 7/1984 | Durkan et al. | 128/200.14 |
| 4,484,578 A | 11/1984 | Durkan | 128/204.24 |
| 4,519,387 A | 5/1985 | Durkan et al. | 128/204.23 |
| 4,567,888 A | 2/1986 | Robert et al. | 128/204.21 |
| 4,575,042 A | 3/1986 | Grimland et al. | 251/46 |
| 4,584,996 A * | 4/1986 | Blum | 128/204.21 |
| 4,612,928 A | 9/1986 | Tiep et al. | 128/204.23 |
| 4,648,395 A | 3/1987 | Sato et al. | 128/204.23 |
| 4,665,911 A | 5/1987 | Williams et al. | 128/204.21 |
| 4,681,099 A | 7/1987 | Sato et al. | 128/204.23 |
| 4,686,974 A | 8/1987 | Sato et al. | 128/204.23 |
| 4,686,975 A | 8/1987 | Naimon et al. | 128/204.23 |
| 4,705,034 A | 11/1987 | Perkins et al. | 128/204.21 |
| 4,706,664 A | 11/1987 | Snook et al. | 128/204.23 |
| 4,744,356 A | 5/1988 | Greenwood | 128/204.26 |
| 4,745,925 A | 5/1988 | Dietz | 128/725 |
| 4,784,130 A | 11/1988 | Kenyon et al. | 128/204.21 |
| 4,823,788 A | 4/1989 | Smith et al. | 128/205.24 |
| 4,827,922 A | 5/1989 | Champain et al. | 128/204.21 |
| 4,873,971 A | 10/1989 | Perkins | 128/201.23 |
| 4,889,116 A * | 12/1989 | Taube | 128/204.23 |
| 4,932,402 A | 6/1990 | Snook et al. | 128/204.23 |
| 4,971,049 A | 11/1990 | Rotariu et al. | 128/204.21 |
| 5,005,570 A | 4/1991 | Perkins | 128/204.23 |
| 5,024,219 A | 6/1991 | Dietz | 128/204.21 |
| 5,038,770 A | 8/1991 | Perkins | 128/204.18 |
| 5,038,771 A | 8/1991 | Dietz | 128/204.21 |
| 5,048,515 A * | 9/1991 | Sanso | 128/204.26 |
| 5,052,400 A | 10/1991 | Dietz | 128/722 |
| 5,074,299 A | 12/1991 | Dietz | 128/204.21 |
| 5,099,837 A | 3/1992 | Russel, Sr. et al. | 128/204.26 |
| 5,103,814 A | 4/1992 | Maher | 128/204.18 |
| 5,137,017 A | 8/1992 | Salter | 128/207.18 |
| 5,165,397 A | 11/1992 | Arp | 128/204.21 |
| 5,251,632 A | 10/1993 | Delpy | |
| 5,280,780 A | 1/1994 | Abel | 128/203.14 |
| 5,282,464 A | 2/1994 | Brain | 128/207.15 |
| 5,315,990 A | 5/1994 | Mondry | 128/205.11 |
| 5,323,776 A | 6/1994 | Blakeley et al. | |
| 5,360,000 A | 11/1994 | Carter | 128/204.26 |
| 5,365,922 A | 11/1994 | Raemer | 128/204.23 |
| 5,388,575 A | 2/1995 | Taube | 128/204.23 |
| 5,398,676 A | 3/1995 | Press et al. | |
| 5,398,682 A | 3/1995 | Lynn | |
| 5,443,062 A | 8/1995 | Hayes | 128/204.26 |
| 5,495,848 A | 3/1996 | Aylsworth et al. | 128/207.18 |
| 5,546,933 A | 8/1996 | Rapoport et al. | |
| 5,558,086 A | 9/1996 | Smith et al. | 128/204.26 |
| 5,582,164 A | 12/1996 | Sanders | |
| 5,603,315 A | 2/1997 | Sasso, Jr. | 128/204.18 |
| 5,752,509 A | 5/1998 | Lachmann et al. | |
| 5,810,759 A * | 9/1998 | Merz | 604/4 |
| 5,865,174 A * | 2/1999 | Kloeppel | 128/204.23 |
| 6,099,481 A | 8/2000 | Daniels et al. | |
| 6,142,149 A | 11/2000 | Steen | |
| 6,186,142 B1 * | 2/2001 | Schmidt et al. | 128/204.23 |
| 6,192,883 B1 | 2/2001 | Miller, Jr. | |
| 6,220,244 B1 | 4/2001 | McLaughlin | |

OTHER PUBLICATIONS

V.K. Bhutani et al., "Adaptive Control of Inspired Oxygen Delivery to the Neonate", *Pediatric Pulmonology*, 14, pp. 110–117 (1992).

S.R. Braun et al., "Comparision of Six Oxygen Delivery Systems for COPD Patients at Rest and During Exercise", *Chest*, 102, pp. 694–698 1992).

B. Celli et al., "Standards for the Diagnosis and Care of Patients with Chronic Obstructive Pulmonary Disease", *Am J Respir and Crit Care Med*, 152, pp. 77–120 (1995).

P. Collins et al., "Apparatus for the Servocontrol of Arterial Oxygen Tension in Preterm Infants", *Med., & Biol. Eng. & Comput.*, 17, pp. 449–452 (1979).

"Continuous or Nocturnal Oxygen Therapy in Hypoxemic Chronic Obstructive Lung Disease", *Annals of Internal Medicine*, 93, pp. 391–398 (1980).

J.E. Cotes, "Continuous Versus Intermittent Administration of Oxygen During Excercise to Patients with Chronic Lung Disease", *The Lancet*, pp. 1075–1077 (1963).

M.J. Decker et al., "Extended Monitoring of Oxygen Saturation in Chronic Lung Disease", *Chest*, 102, pp. 1075–1079 (1992).

B. Make, "Oxygen Therapy", Jewish Center for Immunology and Respiratory Medicine, *Medical/Scientific Update*, 11, (1993).

M. Mecikalski et al., "A Demand Valve Conserves Oxygen in Subjects with Chronic Obstructive Pulmonary Disease", *Chest*, 86, pp. 667–670 (1984).

P.E. Morozoff et al., "Automatic Control of Blood Oxygen Saturation in Premature Infants", *Second IEEE Conference on Control Applications*, pp. 415–419 (1993).

P.E. Morozoff et al., "Closed–loop Control of $Sao_2$ in the Neonate", Biomedical Instrumentation and Technology, 26 pp. 117–123 (1992).

J.T.B. Moyle, "Pulse Oximetry", (BMJ Publishing Group, London), pp. vii,ix,1–134 (1994).

D. B. Raemer et al., "$FI_x$ Controller: An Instrument to Automatically Adjust Inspired Oxygen Fraction Using Feedback Control From a Pulse Oximeter", *Journal of Clinical Monitoring*, 13, pp. 91–101 (1997).

G. Ritchie et al., "Closed–Loop Control of Oxygen Delivery During Aeromedical Evacuation of Patients", *Proceedings of the IEEE Southeast Conference,*–pp. 763–767 (1992).

A. Sano et al., "Adaptive Control of Arterial Oxygen Pressure of Newborn Infants Under Incubator Oxygen Treatments", *IEE Proceedings*, 132, pp. 205–211 (1985).

P. Sliwinski et al., "The adequacy of oxygenation in COPD patients undergoing long–term oxygen therapy assessed by pulse oximetry at home", *European Respiratory Journal*, 7 pp. 274–278 (1994).

R. Smith, "Carrying On: Portable oxygen stands out as a valve–added service to referral sources" *Home Health Care Dealer/Supplier*, pp. 43–44,46 (1997).

F.T. Tehrani et al., "An Automatic Control System for Oxygen Therapy of Newborn Infants", *Annual International Conference of the IEEE Engineering in Medicine and Biology Society*, 13 pp. 2180–2182 (1991).

F.T. Tehrani et al., "A feedback controller for supplemental oxygen treatment of newborn infants: a simulation study", *Med. Eng. Phys.*, 16, pp. 329–333 (1994).

B.L. Tiep et al., "Low–concentration Oxygen Therapy Via a Demand Oxygen Delivery System", *Chest*, 87, pp. 636–638 (1985).

B.L. Tiep, "Future Directions for Long–Term Oxygen Therapy", *Lung Biology in Health and Disease*, pp. 347–362.

D. Weill et al., "Oxygen–Conserving Devices", *Lung Biology in Health and Disease*, 81, pp. 235–256 (1995).

S.W. Weitzner et al., "The Rate of Arterial Oxygen Desaturation During Apnea in Humans", Anesthesiology, 20, pp. 624–627 (1959).

C. Yu et al., "Improvement in Arterial Oxygen Control Using Multiple–Model Adaptive Control Procedures", *IEEE Transactions on Biomedical Engineering*, BMF–34, pp. 567–574 (1987).

* cited by examiner

AUTOMATED CONTROL AND CONSERVATION OF SUPPLEMENTAL RESPIRATORY OXYGEN

FIELD OF THE INVENTION

The present invention relates to the field of supplemental respiratory oxygen supply systems and methods. More particularly, the present invention provides methods and systems that conserve supplemental respiratory oxygen supplied to subacute care patients by continuously measuring blood oxygen content in combination with respiration.

BACKGROUND OF THE INVENTION

A large patient community is currently undergoing oxygen therapy at home or in a long-term care facility, such as a nursing home. Supplemental respiratory oxygen has been a widely accepted form of treatment for COPD (chronic obstructive pulmonary disease) patients with hypoxemia following the completion of a major National Institutes of Health study in 1980. The Nocturnal Oxygen Therapy Trial established the efficacy of continuous oxygen therapy in the extension of the life span of sufferers of COPD with chronic hypoxemia.

For administration of long-term oxygen therapy it has been common practice to deliver the oxygen directly into the nostrils of the patient through a device known as a nasal cannula. The cannula is connected via a supply hose to a source of oxygen, such as an oxygen concentrator, liquid oxygen dewar or high pressure gas cylinder. The oxygen is delivered continuously to the patient at a rate prescribed by a physician.

It has been recognized that continuous oxygen delivery is wasteful of oxygen, as a patient needs oxygen only when they are inhaling and the oxygen delivered at other times is wasted. The most significant financial cost associated with this waste is found in the increased service visits required by the oxygen provider to replenish the patient's oxygen supply, because the actual cost of the oxygen is only a small fraction of the total cost of the therapy.

Another problem associated with supplemental oxygen therapy is that the physical size and weight of the oxygen apparatus can reduce the patient's mobility.

A number of approaches have been taken to address the problems of waste, cost and portability of oxygen therapy. The therapeutic approach that has grown out of this body of work is typically referred to as "demand delivery." The devices respond to a patient's inspiratory effort by delivering a predetermined pulse of oxygen during the period of inhalation, rather than allow the oxygen to flow to the patient continuously. There are many ways in which this basic concept has been implemented.

Extensive work has been done on sensors, timing of oxygen release, and algorithms for delivery of the oxygen. A variety of methods for sensing the respiratory cycle have been used, including pressure sensors that are in fluidic communication with the patient's airway, flow sensors, and chest belts which detect the movement of the thorax during respiration. Some systems deliver a small bolus of oxygen at the beginning of inhalation, while others deliver continuous flow throughout inhalation. There has also been work on the frequency of delivery. For example, some systems do not provide oxygen at every breath.

In spite of the large variety of approaches taken to conserve oxygen supplies and/or reduce the size and weight of the oxygen supply equipment, no consensus has yet been reached as to the most appropriate way to save oxygen and medicate the patient adequately.

The simplest approaches to conserve oxygen involve detection of inhalation as a trigger to deliver oxygen. A variety of detection devices were developed in pursuit of this basic approach to controlling oxygen supply, including a chest belt worn by the patient that generates an electrical signal to trigger the opening of the oxygen supply valve; a hand-activated breathing device attached to a portable gas bottle via a supply hose in which users would dispense the oxygen by pushing a button while holding the device next to their mouth; a mechanical chest strap/valve that functions as both an inhalation sensor and delivery device in an oxygen conserving system; and an all-pneumatic, fluidically-controlled device.

Another approach uses pressure sensors in the oxygen line to monitor line pressure at the nostrils. A small negative pressure, indicative of the onset of inhalation, triggers the release of oxygen. This type of detection scheme has become the standard method and is employed by most systems currently in use. The systems attempt to provide a physiologically equivalent dose of oxygen, when compared to continuous flow, by providing a burst of oxygen at the onset of inhalation. By providing more oxygen at the beginning of inhalation, when it is more physiologically useful, the most efficient of these systems claim to be able to reduce oxygen consumption.

The existing demand delivery devices provide economic benefit in the form of oxygen savings (and reduced service visits), but it is often at the expense of the level of medical care. In particular, some patients have been found to have deficient levels of oxygen in their blood as a result of using known demand delivery devices. Certain activities, such as exercise and sleep, cause the body's need for oxygen to fluctuate in an unpredictable manner. The chronic hypoxemia being corrected by the prescription of oxygen therapy is not fully ameliorated by these devices.

Because demand delivery devices and continuous flow systems do not measure the patient's blood oxygen saturation, they do not respond to a change in patient need as would be indicated by a drop in oxygen saturation. The oxygen flow in the form of pulses of gas is fixed in some devices, such as the PulseDose by DeVilbiss, as it is delivered with every breath. In other devices, such as the Oxymatic 301 from Chad Therapeutics, the patient is allowed some adjustability in the flow by determining the frequency of pulses as a function of the number of breaths; i.e., one pulse every fourth breath, a pulse every other breath, etc. None of these types of demand delivery system is capable of directly addressing fluctuations in the blood oxygen level experienced by the user.

In fact, while it is generally known that existing modes of oxygen therapy are inadequate for most patients at least some of the time (that is, acute periods of hypoxia, $SaO_2 < 88\%$, can be seen in virtually all patients for some fraction of each day), another problem that is not addressed by the known devices and methods is that the average COPD patient is receiving more oxygen than needed for a significant part of each day. For example, the oxygen patients studied by Decker, et al. (Chest 1992) had an $SaO_2$ greater than 90% for more than 70% of the time they spent breathing room air without any supplemental oxygen. In another study of even sicker patients (Sliwinski, et al., European Respiratory Journal 1994), $SaO_2$ was greater than 88% for 40% of the time while breathing room air, and greater than 92%

(higher than necessary) for about 70% of the time they were using their supplemental oxygen. The lack of methods and/or systems for controlling the upper limit of blood oxygen content results in significant amounts of wasted oxygen.

As discussed above, existing demand delivery devices conserve oxygen by delivering oxygen only during inhalation. Most of these devices provide a very short pulse of oxygen immediately after the onset of inspiration. The savings is derived from the fact that these pulses of oxygen are physiologically equivalent to the standard continuous flow prescription.

Devices which control the flow of oxygen based on blood oxygen measurements from various types of sensors have been described for a variety of applications. However, none of these devices were meant for residential use by sub-acute COPD patients, none had the goal or object of conserving as much oxygen as possible while still maintaining a healthy blood oxygen level, and none used a pulsed, demand-delivery method for conserving oxygen.

Measurements of blood oxygen saturation can be broken into two groups of measurement strategies: invasive and non-invasive. An invasive measurement using existing technology requires that blood be drawn from the body and the sample placed in a blood gas analyzer. One common non-invasive blood oxygen sensor is a pulse oximeter which relies on the differences in the light absorption curves of saturated and desaturated hemoglobin in the infrared and near-infrared portions of the spectrum. The typical pulse oximeter sensor includes two LED's, one red and one infrared. As the light from the two LED's passes through a capillary bed at the point of attachment, such as is found on the finger, the light is partially absorbed by the blood and tissues and then is detected by a photodetector. The electrical signal generated by the photodetector, which is proportional to the amount of light absorbed by the body, is transmitted to the oximeter. The absorption measurements can be made rapidly, up to 500 times per second for each LED. Because of the pulsatile nature of arterial blood, the absorption as a function of time will vary slightly at the frequency of the pulse. This allows the oximeter to extract the arterial blood oxygen saturation information from background noise caused by absorption in tissues located between the LED's and the photodetector. Pulse oximetry is a well-accepted technique and can be found in machines used for monitoring patients under anesthesia, patients participating in sleep studies and neonatal monitoring.

Some methods and systems for controlling oxygen delivery to patients in critical care settings have been disclosed. Some of the systems use feedback loop controllers that use the blood oxygen saturation signal, $SpO_2$, from a pulse oximeter to control the inspired oxygen fraction ($FIO_2$) in the respiratory gas delivered by a mechanical ventilator in which oxygen is mixed with air to supply an accurate amount of oxygen to a patient through a mask or hood. These systems are intended for the care of critically ill patients receiving treatment in hospitals for severe respiratory distress caused by a chronic condition or accident.

SUMMARY OF THE INVENTION

The present invention provides demand respirating oxygen supply methods and systems which maintain healthy blood oxygen saturation in sub-acute patients receiving supplemental oxygen through a nasal cannula by controlling the dosing of oxygen with a measured response to the patient's actual blood oxygen saturation levels. This closed-loop control of oxygen flow for COPD patients provides for both healthy blood oxygen levels and significant oxygen conservation. In various embodiments of the invention, a control circuit responsive to sensor inputs operates a valve to supply respiratory oxygen to an in vivo respiratory system.

In one aspect, the present invention provides a method of controlling supplemental oxygen delivery for sub-acute care in a residential setting by continuously measuring blood oxygen content of a sub-acute patient in a residential setting; determining when the patient is inhaling; delivering supplemental oxygen from an oxygen source to the patient through a nasal cannula when the patient is inhaling if the measured blood oxygen content is below a desired level; and preventing oxygen delivery from the oxygen source to the patient if the measured blood oxygen content of the patient is above a desired level.

In another aspect, the present invention provides a method of controlling supplemental oxygen delivery for sub-acute care in a residential setting by continuously measuring blood oxygen content of a sub-acute patient in a residential setting with a pulse oximeter; determining when the patient is inhaling; delivering supplemental oxygen from an oxygen source to the patient through a nasal cannula when the patient is inhaling if the measured blood oxygen content is below a desired level; preventing oxygen delivery from the oxygen source to the patient if the measured blood oxygen content of the patient is above a desired level; determining if the blood oxygen content measured by the pulse oximeter is invalid; delivering a default amount of supplemental oxygen to the patient when the measured blood oxygen content is invalid for a predetermined time; determining when the measured blood oxygen content is valid after having been determined invalid; and resuming delivery of supplemental oxygen from an oxygen source to the patient if the measured blood oxygen content is below the desired level.

In another aspect, the present invention provides a method of controlling supplemental oxygen delivery for sub-acute care in a residential setting by continuously measuring blood oxygen content of a sub-acute patient in a residential setting; determining when the patient is inhaling; and delivering a variable dose of supplemental oxygen from an oxygen source to the patient through a nasal cannula when the patient is inhaling, wherein the variable dose is at least partially determined based on the measured blood oxygen content.

In another aspect, the present invention provides a method of controlling supplemental oxygen delivery for sub-acute care in a residential setting by continuously measuring blood oxygen content of a sub-acute patient in a residential setting; determining when the patient is inhaling; delivering a variable dose of supplemental oxygen from an oxygen source to the patient through a nasal cannula when the patient is inhaling, wherein the variable dose is at least partially determined based on a difference between the desired blood oxygen content and the measured blood oxygen content and a trend in measured blood oxygen content; and further wherein the variable dose includes a zero dose; determining if the measured blood oxygen content is invalid; delivering a default amount of supplemental oxygen to the patient when the measured blood oxygen content is invalid for a predetermined time; determining when the measured blood oxygen content is valid after having been determined invalid; and resuming delivery of the variable dose of supplemental oxygen from the oxygen source to the patient based at least partially on the measured blood oxygen content.

In another aspect, the present invention provides a system for controlling supplemental oxygen delivery for sub-acute care in a residential setting including means for continuously measuring blood oxygen content of a sub-acute patient in a residential setting; means for determining when the patient is inhaling; means for delivering supplemental oxygen from an oxygen source to the patient through a nasal cannula when the patient is inhaling if the measured blood oxygen content is below a desired level; and means for preventing oxygen delivery from the oxygen source to the patient if the measured blood oxygen content of the patient is above a desired level.

In another aspect, the present invention provides a system for controlling supplemental oxygen delivery for sub-acute care in a residential setting including means for continuously measuring blood oxygen content of a sub-acute patient in a residential setting; means for determining when the patient is inhaling; and means for delivering a variable dose of supplemental oxygen from an oxygen source to the patient through a nasal cannula when the patient is inhaling, wherein the variable dose is at least partially determined based on the measured blood oxygen content.

These and other features and advantages of the present invention will be apparent upon review of the detailed description of the invention and accompanying drawings.

DETAILED DESCRIPTION OF THE INVENTION

Figure 1:
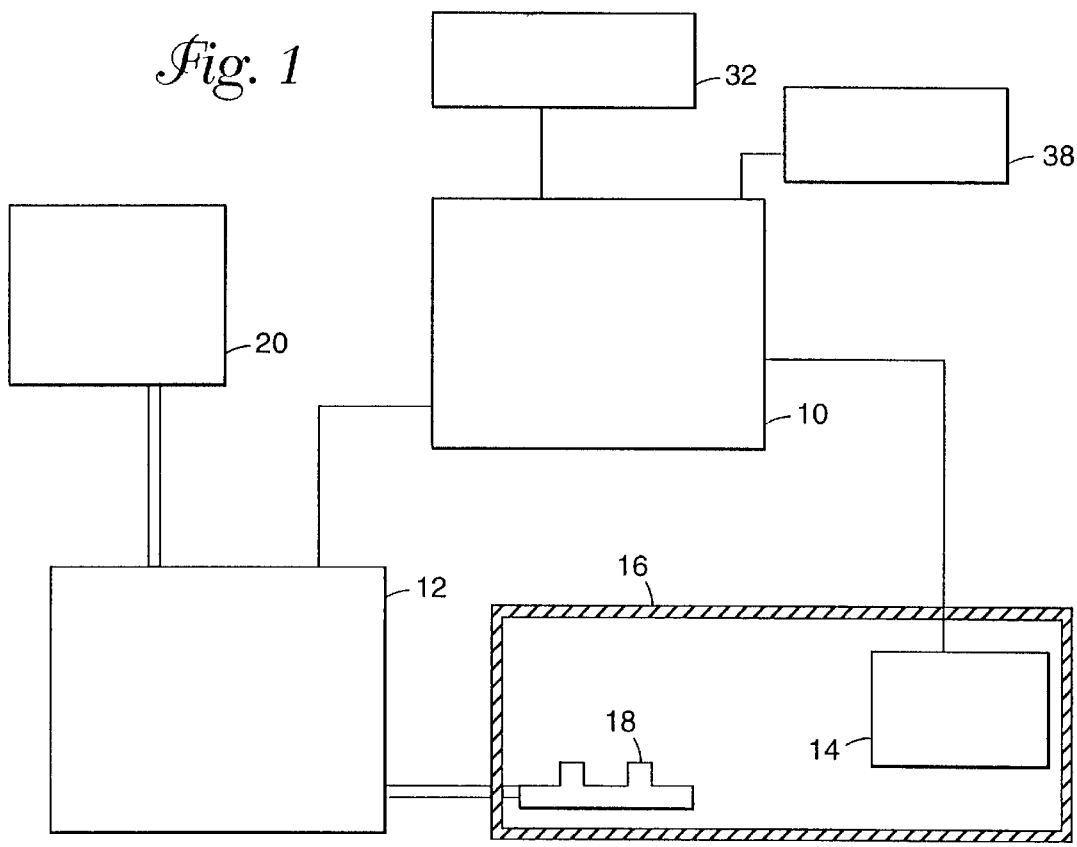
FIG. 1 is a schematic diagram of one system according to the present invention.

As described above, the present invention provides demand respirating oxygen supply methods and apparatus for use in sub-acute care which maintain healthy blood oxygen saturation in patients by controlled dosing of oxygen with a measured response to the patient's actual blood oxygen content. The dosing can be provided by simple ON/OFF control over the delivery of oxygen or the amount of oxygen delivered to the patient with each inhalation can be varied in response to the patient's need as determined by a more sophisticated control scheme, such as a PID loop control algorithm, that utilizes the difference between the patient's actual blood oxygen content and a target blood oxygen content.

The systems and methods of the present invention are particularly directed at patients receiving supplemental oxygen in a sub-acute care environment. As used in connection with the present invention, sub-acute care includes the delivery of supplemental oxygen, typically through a nasal cannula, to a patient in a residential setting and/or in ambulatory situations, i.e., when the patient is engaged in normal activities outside of his or her residence such as shopping, etc.

The needs and considerations of patients receiving supplemental oxygen in sub-acute care differ from those present when providing oxygen to patients in critical care environments, e.g., hospitals or other medical facilities, in which the amounts of oxygen delivered are carefully controlled in connection with masks or other enclosures. In those situations, the fractional amount of inspired oxygen ($FIO_2$) is typically controlled by mixing oxygen and air in a blender or other device before delivering the gas to the patient.

Among the advantages of the present invention are the significant conservation of oxygen provided by delivering only the amount of oxygen needed to maintain a healthy blood oxygen content and the ability to address therapeutic problems associated with demand delivery systems by providing the correct amount of oxygen to the patient to reduce uncontrolled hypoxic events.

The amounts of oxygen that can be conserved by implementing the methods according to the present invention can be significant, even compared to known demand delivery systems that conserve oxygen by simply turning the supply on or off during a patient's respiration. Studies have reported oxygen savings ratios of from 3:1 to 7:1 for known simple demand delivery systems. Implementation of the methods according to the present invention by using a demand delivery approach with a feedback control mechanism that responds to a continuous blood oxygenation measurement could provide an oxygen savings ratio of greater than 13:1 while maintaining the patient's $SaO_2$ at the 90% level.

Other advantages of the methods and apparatus according to the present invention are the ability to integrate the invention with any sub-acute care supplemental oxygen supply system, including both ambulatory and stationary sources. For unlimited volume sources, such as oxygen concentrators and membrane separators, the invention will reduce their size and energy consumption for a given level of therapy. For fixed volume gas sources, such as liquid and high pressure gas, the invention will extend the lifetime of the oxygen supply, thereby significantly decreasing the cost of providing that treatment.

If the system is ambulatory, the present invention can allow for reductions in the size and weight of the oxygen source, thereby increasing the patient's mobility. An added benefit of reducing the size and/or weight of the ambulatory systems is the potential for a better therapeutic outcome. If patients find the smaller, lighter weight systems less cosmetically unattractive they will be more likely to carry and use the systems during ambulatory activities as opposed to not using the systems. Studies have shown that the benefit of supplemental oxygen systems is significantly reduced if the systems are not used on a regular basis.

Another advantage of the invention, method and apparatus, is a reduction in the risk of hypercapnia (carbon dioxide retention) by only providing enough oxygen to reach a predetermined blood oxygen saturation, typically about 90% as measured by a conventional two-color pulse oximeter.

One embodiment of an automated respiratory oxygen supply system is depicted in FIG. 1 and includes a controller 10, a demand delivery module 12, and a blood oxygen content sensor 14 connected to the patient 16. Oxygen is supplied from an oxygen source 20 to the patient 16 by the demand delivery module 12 through, in the preferred embodiments, a nasal cannula 18. The preferred system can also include a user interface 32 and an alarm 38.

Oxygen source 20 could be an oxygen concentrator, membrane separator, high pressure cylinder or liquid oxygen dewar. This could also include any portable versions of oxygen sources 20. Other potential sources of oxygen gas suitable for providing supplemental oxygen in sub-acute care in a residential setting and/ambulatory situations may be created in the future and should be considered as being functional with the described invention. As used below, "line" will refer to any connection made between the oxygen source, the described invention and the patient.

If the oxygen source 20 is an oxygen concentrator, typically a continuous low-flow device, usually delivering at most 6 liters/min of 96% oxygen, the system may also include an oxygen storage device to accommodate the periodic higher flows that are necessary to practice the methods described below. If high flow concentrators become available, such a storage device would not be needed.

One preferred controller 10 is an electronic circuit including a software programmable microcontroller as its main component. Depending on the allocation of tasks within the device a number of microcontrollers could be used as a controller 10. In the preferred embodiment, the controller 10 includes a serial data input port, LED driver capabilities and digital I/O pins. One example of a suitable controller is the PIC16C6X family of microcontrollers from Microchip Technology Inc. of Chandler, Ariz.

Those skilled in the art will realize that a great deal of optimization may be done relative to the choice of a microcontroller(s). Specifications, such as power consumption, cost, memory size, clock speed and part availability may alter the choice for a preferred microcontroller. Furthermore, many of the functions described for the microcontroller in the preferred embodiment could be accomplished by using discrete circuits of many types. Additionally, the microcontroller and its peripheral circuitry may be replaced entirely by discrete circuitry, such as programmable logic arrays, A/D converter chips, analog comparators, etc.

The system also includes an oxygen content sensor 14 for monitoring the blood oxygen content of the patient 16. This information is then fed back to the controller 10 for use in executing the methods according to the present invention. It is preferred that the oxygen sensor 14 provide a signal to the system controller 10 in the form of a blood oxygen saturation in percent. The sensor 14 preferably processes all of its data internally and the controller 10 preferably processes only error flags and numerical information as described shortly.

One preferred oxygen sensor 14 is a non-invasive sensor such as a two-color pulse oximeter. As used herein, the terms "pulse oximeter" or "oxygen sensor" will include both the optical sensor and the circuitry used to determine blood oxygen saturation levels using the optical sensor. One example of a suitable pulse oximeter is a conventional two-color, OEM oximeter module, from Nonin Medical Inc. of Plymouth, Minn., that can measure the percentage of oxygen-saturated hemoglobin, $SpO^2$, in the blood stream of an in vivo respiratory system. The preferred embodiment of the pulse oximeter 14 uses a transmitting sensor that attaches to the user's finger. Alternative embodiments may employ sensors that attach elsewhere on the body.

While the pulse oximeter is one preferred non-invasive oxygen sensor, it should be understood that any blood oxygen sensor useful for determining blood oxygen content on a continuous basis could be used in connection with the present invention. Any such alternative could be correlated to e.g., blood oxygen measurements of a carbon monoxide-oximeter (CO-oximeter). A CO-oximeter is a bench-top, laboratory device which requires a sample of blood that has been drawn from the patient. It uses optical absorption measurements at several wavelengths to determine the oxygen content of blood. Blood oxygen levels can also be referred to by the term "partial pressure of oxygen." Partial pressures of oxygen, $PaO_2$, are measured using an electrochemical cell and a sample of blood which has been drawn from the patient. There are standard curves that relate blood oxygen saturation, $SaO_2$, to partial pressure of oxygen in the blood, $PaO_2$. The methods and systems of the described device operate independently from the method of determining the oxygen content of the blood. Furthermore, as used herein, the terms "blood oxygen content" or "blood oxygen level" are to be considered equivalent to "blood oxygen saturation."

It should also be apparent to those skilled in the art that technologies on the horizon, such as an implantable, microelectromechanical (MEMS) blood gas analyzer, may provide the blood oxygen content information needed by the system controller 10. Furthermore, there may be improvements in pulse oximetry technology, such as the ability to determine the level of carboxyhemoglobin in the blood, that may be useful for the described invention. Use of these new blood oxygen content technologies in oxygen conservers for long-term oxygen therapy should be considered to lie within the scope of the systems and methods of the present invention provided they have the ability to provide continuous blood oxygen content measurements.

In the preferred embodiment, the pulse oximeter 14 deconvolves the optical information into a blood oxygen saturation value, $SpO_2$, in percent. The oximeter 14 outputs a serial data stream with this information to the controlling means 10 for evaluation. Other important information is also included in the oximeter data stream, such as the user's pulse rate and error handling information that details the reliability of the $SpO_2$ and pulse rate values. It will be recognized by those skilled in the art that an alternative embodiment may be provided in which the system controller 10 is the oximeter and that the data evaluation and error handling would be accomplished internally to the system controller 10 with an appropriate optical sensor being attached to the patient 16.

Blood oxygen content measuring in connection with the present invention is described as "continuous" although it will be understood that the measurements made using, e.g., pulse oximeters and other devices, may actually be taken at discrete intervals. By "continuous" as used in connection with the measuring of blood oxygen content in the present invention, it is meant that the blood oxygen content of the patient will be measured at intervals (fixed or variable) that are sufficiently small to provide the advantages of the invention. Preferably the sampling intervals will be less than about five minutes, more preferably less than about one minute, and even more preferably less than about one respiration interval (i.e., the time between the onset of two inhalations by the patient).

The information relating to blood oxygen content provided by the oxygen sensor 16 is then used by the system controller 10 in combination with the demand delivery module 12 to provide control over the oxygen supplied to the patient 16 from the oxygen source 20 as described in connection with the methods according to the present invention below.

Figure 2:
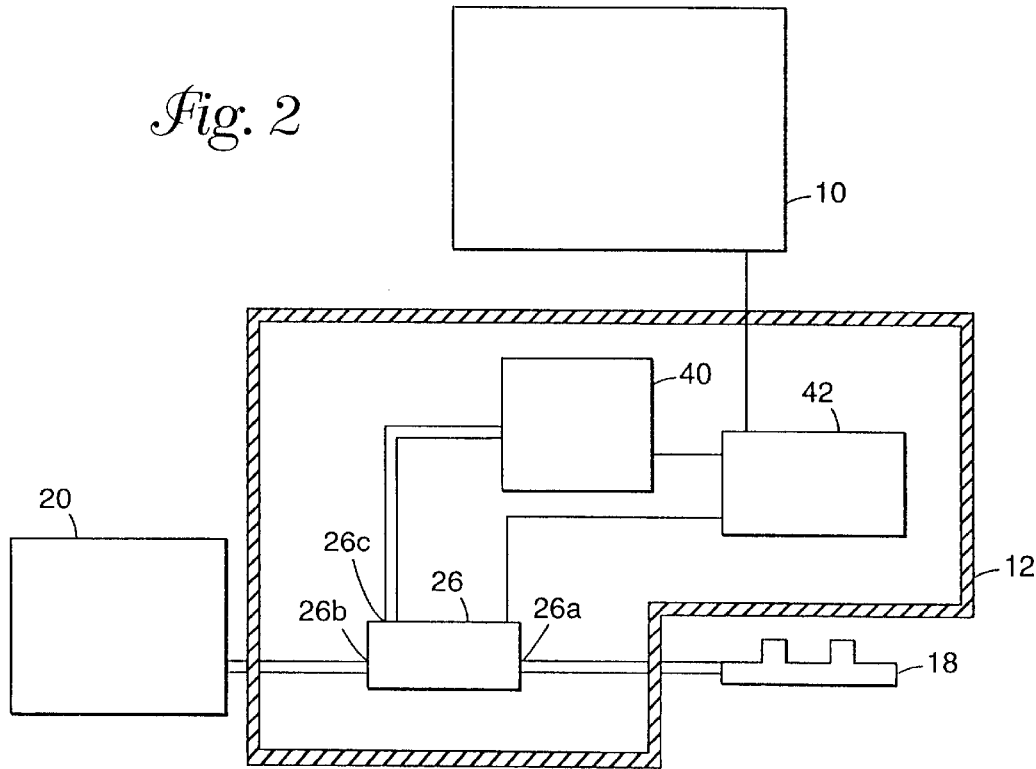
FIG. 2 is a schematic diagram of one demand delivery module for use in a system such as that depicted in FIG. 1.

A block diagram illustrating the components of one embodiment of a demand delivery module 12 according to the present invention is depicted in FIG. 2. One component in the demand delivery module 12 is an inhalation or respiration sensor 40 that monitors the respiratory activity of the patient 16 to determine when inhalation is occurring. In one preferred embodiment, the inhalation sensor 40 provides a signal to an inhalation sensor and valve controller 42 that, in turn, controls the valve 26 based on additional input from system controller 10 (as will be described in more detail below). The inhalation sensor 40 can take a variety of forms that will be known to those skilled in the art. One type of suitable inhalation sensor 40 would monitor flow in the line used to supply oxygen to the nasal cannula 18. The sensor 40 in FIG. 2 monitors flow through the valve 26 interposed in the line between the nasal cannula 18 and the oxygen source 20. One suitable flow sensor is a Honeywell AWM3300 Microbridge Mass Airflow Sensor (available from Honeywell Corp., Minneapolis, Minn.), which can sense flows as small as 10 cc/min, which is about 1 part in 5000 to 10,000 of the peak tidal flow in any given breath.

In addition to this particular flow sensor, it should be understood that other types of sensors may be utilized to detect inhalation and achieve operation of the system. Those skilled in the art will recognize that pressure transducers, thermistors or infrared detectors may all be used to sense inhalation. In one example, a pressure transducer with the appropriate sensitivity, such as a solid-state piezoresistive, capacitive or electromechanical device, could be used to generate an electrical signal in response to the breathing cycle. In another example, thermistors could be used to detect the inward airflow due to inhalation. If the thermistor was sufficiently sensitive, one may be able to ascertain the onset of inhalation by monitoring the temperature of a thermistor (or thermocouple) placed near the nostril. A flow measurement may also be possible with the use of two thermistors in an anemometer configuration. Infrared detectors, such as single element bolometers, could be used as well if they possess the speed and accuracy to distinguish the onset of inhalation. There may be future developments in the arena of flow and pressure sensors that may also be used in connection with the present invention. The electrical signal generated by the preferred inhalation sensor 40 is analog in nature and provides an amplified analog output, 0 to 5V. In the depicted embodiment, the signal from the inhalation sensor 40 is presented to the inhalation sensor and valve controller 42 which compares the analog signal to a programmable voltage reference. A comparator identifies the onset of inhalation by triggering when the sensor output has reached a preset level that represents a specific magnitude of inward flow. The inhalation sensor and valve controller 42 then provides a signal to position the spool of valve 26 so oxygen flows from supply 20 to patient 16 via cannula 18. Sensor and valve controller 42 will maintain the valve spool in this position for a period of time, the "dose time" (D), as specified by the system controller 10. In this manner, a dose of oxygen of duration D can be provided upon the onset of inhalation.

One preferred valve 26 of the embodiment of FIG. 2 is a three-way, two-position, solenoid-actuated spool valve having three ports 26a, 26b, 26c. Port 26a is connected to the in vivo respiratory system of the patient 16 by, e.g., a conventional nasal cannula including a hose plus nares for both nostrils. A known alternative to a nasal cannula is a transtracheal tube for those sub-acute patients that have undergone a tracheotomy. Port 26b is connected to the oxygen source 20 and port 26c is connected to inhalation sensor 40. One preferred valve 26 is manufactured by The Lee Company, of Westbrook, Conn., Model LDHA1213111H.

When oxygen is not being supplied to the patient 16, the spool of the valve 26 is positioned such that ports 26a and 26c are connected so that the inhalation sensor 40, nasal cannula 18, and patient 16 are in fluid communication. This allows the respiratory effort of the patient 16 to be detected by the inhalation sensor 40, through the monitoring of the flow generated in the nasal cannula by inspiratory and expiratory efforts. To supply oxygen to the patient 16, the spool of the valve 26 is moved so as to connect ports 26a and 26b; this, in turn, allows for flow of respiratory oxygen to the patient 16 from supply 20.

In one preferred embodiment, supply 20 is a high pressure gas source and regulator. It is conventional in the medical oxygen business that the regulator is set to 20 psi. With the preferred valve 26, at the given operating pressure of 20 psi, the flow rate through valve 26 will be approximately 0.200 ml/msec. Existing demand delivery devices work with similar valves and flow rates and deliver a 35 ml dose of oxygen in approximately 175 msec. However, there exist many valves that may be used to address issues, such as operating pressures, power consumption, and flow rates, that relate to specific design issues associated with other possible oxygen supply systems.

The preferred embodiment of the demand delivery module 12 in this invention is a subsystem that communicates to and receives communication from system controller 10. More specifically, it receives continually updated values of the dose time D. It will be understood, however, that those skilled in the art could design a demand delivery module 12 which is more or less dependent on the system controller 10 than is described in this embodiment. In particular, it would be possible to construct a system where inhalation sensor 40 provides a signal directly to the system controller 10 if no inhalation sensor and valve controller 42 is provided separately. The controller 10 would then provide a control signal to valve 26 directly. The inhalation sensor and valve controller 42 is useful, however, for another aspect of the present invention which includes the detection of apnea (as will be described more fully below). One suitable inhalation sensor and valve controller 42 is the PIC16C62X series of microcontrollers from Microchip Technology Inc. of Chandler, Ariz. However, it will be apparent to those skilled in the art that a similar demand delivery module 12 could be built without a microcontroller.

Moreover, it should be understood that alternative designs for the connections of the valve 26, inhalation sensor 40, oxygen source 20, and patient 16 may be envisioned by the those skilled in the art. It would be possible to design a system in which an in-line flow sensor and/or three-port, two-way valve are not required. For example, the designs may involve a plurality of valves and sensors. It should be understood that the methods and systems of the described device operate independently from the specific configuration of hardware used for sensing inhalation and the specific valve configuration used to control the flow of oxygen.

Figure 3A:
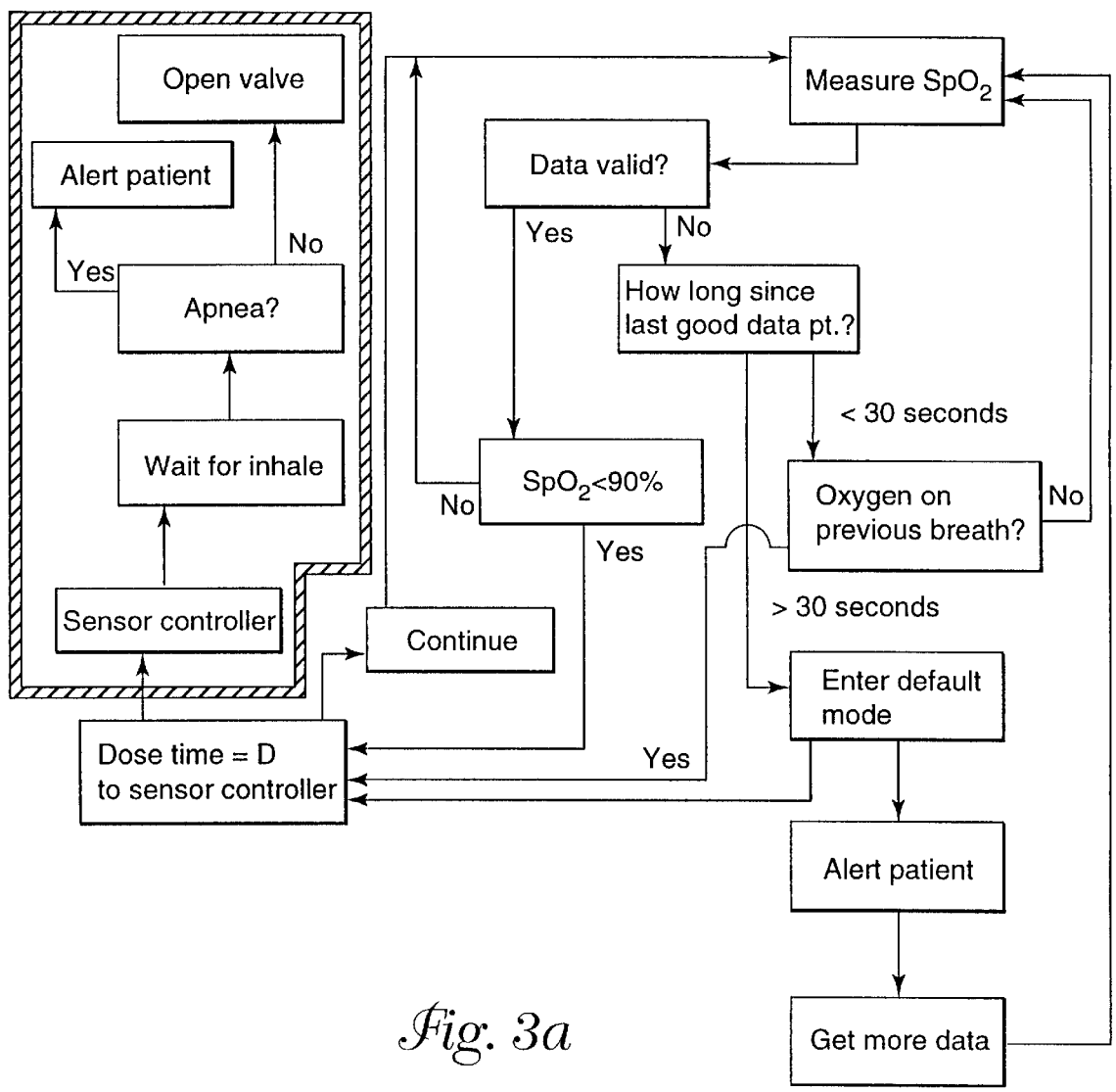
FIG. 3a is a flow diagram of one method according to the present invention.
Figure 3B:
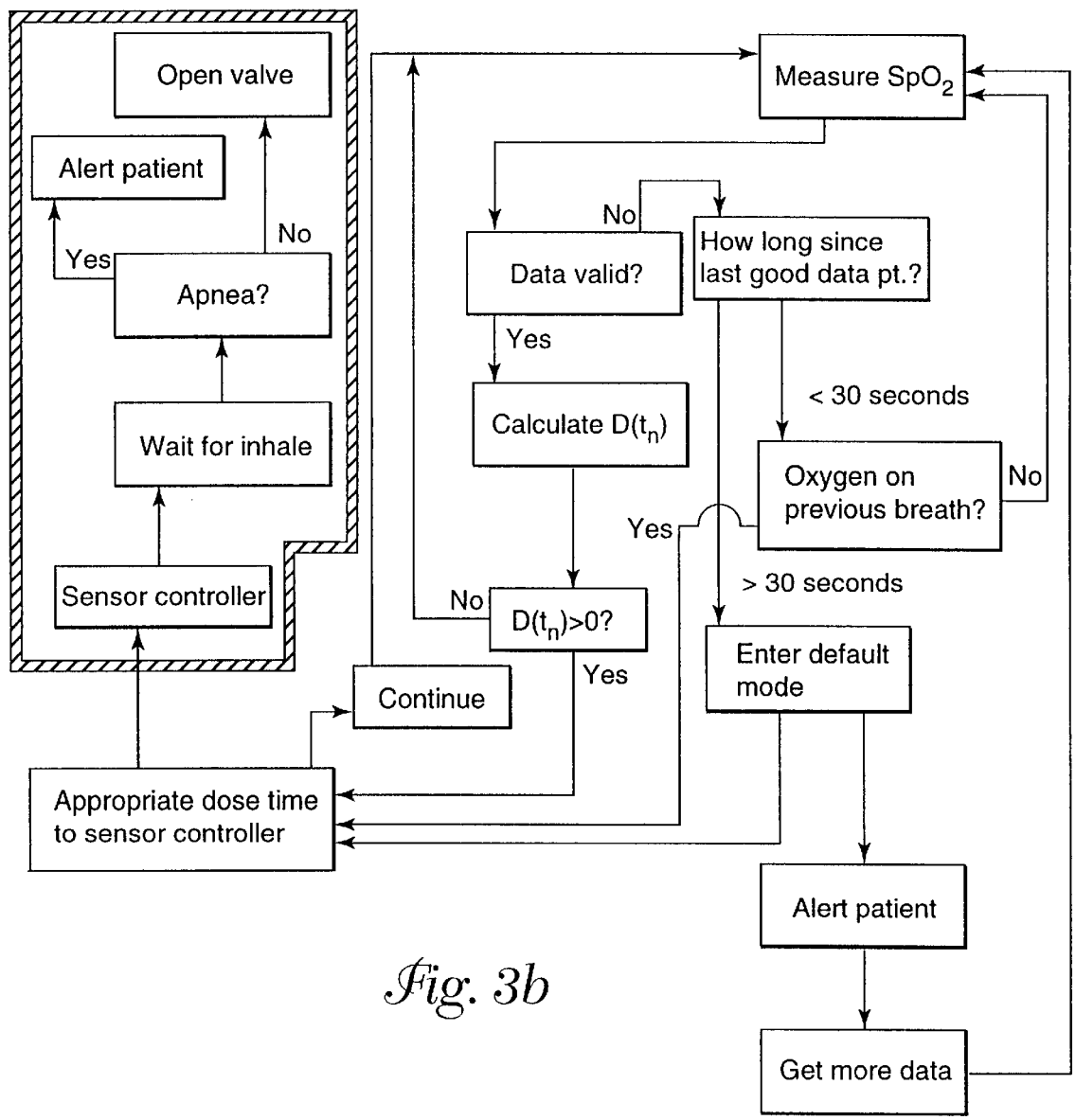
FIG. 3b is a flow diagram of another method according to the present invention.

As long as the data from the blood oxygen content sensor 14 is valid (as described in detail below), the controller 10 uses the data in a control algorithm as illustrated in FIGS. 3a and 3b. The feedback control in the preferred embodiment is implemented as a portion of software code contained in the controller 10; however, it could alternatively be a hardwired controller or combination of hardware and software in other embodiments.

There exist a variety of control methods that are of utility in the present method and invention. The goal of any control method is stable operation of the controlled system about a setpoint. In the preferred embodiment, the setpoint is a blood oxygen saturation ($SpO_2$) of 90%. One control algorithm, the ON/OFF method, is diagrammed in FIG. 3a. When the patient's blood oxygen content is above the setpoint no oxygen is delivered, and when it is below the setpoint oxygen is delivered. More specifically, when the blood oxygen content is above the setpoint, controller 10 sends a dose time of zero (D=0) to the sensor and valve controller 42. When the blood oxygen content falls below the setpoint, controller 10 outputs a non-zero value (D>0) to valve controller 42. As long as the blood oxygen content remains below the setpoint, sensor and valve controller 42 provides a dose of duration D immediately upon the onset of an inhalation. In the simplest implementation, the "ON" dose time D could be a very large time, so that the "ON" mode is essentially equivalent to a continuous flow of oxygen. Alternately, D could be equal to or shorter than a typical inhalation period, in which case the inhalation and valve controller 42 would provide one or more pulses of duration D synchronized with each inhalation (demand mode). The ON/OFF control approach is analogous to the operation of a furnace using a mercury switch thermostat: It is either ON or OFF.

The feedback control algorithm of the preferred embodiment uses a Proportional-Integral-Derivative (PID) loop as illustrated in FIG. 3b. Other embodiments could use algorithms based on fuzzy logic, look-up tables, P or PI loops or increment/decrement methods (oxygen delivery that increases or decreases in a preprogrammed fashion relative to setpoint and/or trend). The PID algorithm is fundamentally different from the simple ON/OFF controller in that it uses both the current value of the blood oxygen content and also trend information to determine oxygen flow. Because of the use of trend information, a system controlled with a PID loop will, at times, deliver oxygen to the patient even if their blood oxygen content is above the setpoint; or, at other times, it may not deliver oxygen even if they are below the setpoint. An example of when this might occur is when the patient's blood oxygen content was above the setpoint but was also dropping very quickly. In this case, the PID loop would start oxygen delivery before the blood oxygen content actually fell below the setpoint. (The ON/OFF method would not start oxygen delivery until after the blood oxygen content was below the setpoint). This enables the PID controller to more effectively minimize the fluctuations of the blood oxygen content about the setpoint.

The preferred systems for implementing the methods of the present invention use a digital controller. As a result, discretization of the general, continuoustime PID equation, Equation 1, must be done, $$D(t) = K_p * [e(t) + (1/T_i) * \int e(t)dt + (T_d) * de/dt] \quad (1)$$

where $D(t)$ is the oxygen dose time, $K_p$ is the loop proportional gain, $T_i$ is the integral time, $T_d$ is the derivative time and T is the period of the measurement. The preferred embodiment utilizes a first order discretization of the continuous time PID equation. This can be seen in Equation 2, $$D(t_n) = D(t_{n-1}) + A_0 e(t_n) + A_1 e(t_{n-1}) + A_2 e(t_{n-2}) \quad (2)$$

where $D(t_n)$ is the control signal (oxygen dose time) generated for time period $t_n$, $e(t_n)$ is the difference between the desired level of blood oxygen saturation (the setpoint) and the measured level at time $t_n$. The coefficients, $A_0$, $A_1$, and $A_2$ are given by Equations 3–5 below:

$$A_0 = -K_p * (1 + t_n/t_i + t_d/t_n) \quad (3)$$

$$A_1 = K_p * (1 + 2 * t_d/t_n) \quad (4)$$

$$A_2 = K_p * (t_d/t_n) \quad (5)$$

where $K_p$ is the loop proportional gain, $t_i$ is the integral time, $t_d$ is the derivative time and $t_n$ is the period of the measurement (0.33 seconds if using the preferred oximeter).

As mentioned, the quantity $e(t_n)$ is the difference between the $SpO_2$ value at time $t_n$ and the setpoint. In the preferred embodiment, a fixed setpoint of $SpO_2 = 90\%$ is used. The control algorithm will specify doses of oxygen in order to maintain the blood oxygen saturation at this level. It is thought that this saturation level may provide the necessary correction to the patient's hypoxemia, while at the same time conserving the greatest amount of oxygen. It should be apparent to those skilled in the art that the desired level (setpoint) can be changed to achieve different therapeutic and economic goals.

Moreover, a system that uses additional physiological parameters, such as pulse rate or respiratory rate, in addition to blood oxygen content as determined by the oxygen sensor to determine a target blood oxygen level (setpoint) that changes on a rolling basis could also be implemented. For example, one may use the heart rate to monitor the patient's activity level and therefore anticipate increased or decreased need of oxygen and adjust the setpoint accordingly. Such schemes would be seeking to ameliorate the possible increased/decreased hypoxemia caused by a change in physical activity level. Such changes to the setpoint should be considered to be within the spirit and scope of the present invention.

Referring now to Equations 3–5 above, the transfer function coefficients $A_0$, $A_1$ and $A_2$ are determined by the settings of loop proportional gain $K_p$, the integral time $t_i$, the derivative time $t_d$ and the time between data points $t_n$. The determination of these values will typically be accomplished through clinical monitoring of COPD patients while the system is in use. The specific values of these loop parameters will depend on design goals such as loop stability, overshoot, time-to-achieve-control, and accuracy. Methods for obtaining values which provide for effective operation of the control loop will be known to those skilled in the art.

In the preferred embodiment, the control signal $D(t_n)$ is the dose time needed to maintain the blood oxygen level at the setpoint. The dose time signal is provided by controller 10 to sensor and valve controller 42. It is the duration of time that valve 26 will be held in the position which permits oxygen to pass from supply 20 to patient 16 via nasal cannula 18 (see FIGS. 1 and 2). A dose of oxygen of duration $D(t_n)$ is provided immediately after the onset of inhalation (as indicated by inhalation sensor 40 and sensor and valve controller 42, described previously). It should be understood that other methods besides varying the dose time could also be employed to control the patient's blood oxygen content. For example, a system which includes a variable-flow valve (as opposed to the preferred, open/closed valve) could be constructed. In such a system, the controller 10 could specify the oxygen flow level. The specified flow could, in turn, be provided for a fixed period of time at the onset of each breath, or continuously. Alternately, the blood oxygen content could be controlled by providing a dose of oxygen on one or more sequential breaths and then delivering no oxygen on one or more subsequent breaths. In this method, the control parameter could be described as the number of breaths during which oxygen is or is not delivered. It should be understood that those skilled in the art could construct a control scheme which uses any of these alternate methods or a combination of these methods.

The controller 10 should also have a minimum limit (Dmin) for the dose time. If the dose time $D(t_n)$, as determined by Equation 2, is less than Dmin, a dose time of Dmin will be used instead. In one preferred embodiment, Dmin will be zero. The dose time $D(t_n)$ determined by Equation 2 will, at times, be negative. This will primarily occur when the patient's blood oxygen content is greater than the setpoint. Since a negative dose time is not physically meaningful, the controller will instead substitute a dose time of Dmin. Of course, Dmin could also be greater than zero.

Similarly, in one preferred embodiment the controller 10 would also have a maximum limit (Dmax). If the dose time $D(t_n)$, as determined by Equation 2, is greater than Dmax, a dose time of Dmax is used instead. In one preferred embodiment, Dmax is equal to twice the default dose (described in detail below). This prevents the application of excessive amounts of oxygen and thus minimizes the patient's risk of hypercapnia (carbon-dioxide retention). Those skilled in the art will appreciate that other values of Dmax could also be used.

In any system and method according to the present invention, the ability to respond to periods of invalid or bad data in the blood oxygen content measurements must be provided. In the preferred methods and systems, the delivery of oxygen moves from the closed loop control described herein to open loop control based on the criteria described herein (i.e., default values, interpolated data, etc.) and back to closed loop control when the blood oxygen measurements are again valid. In other words, the methods/systems according to the present invention will determine when the blood oxygen content data is invalid, deliver a default amount of oxygen during periods of invalid data, and then resume delivery of supplemental oxygen based on blood oxygen content when that data is again valid. The ability of the systems and methods of the present invention to move from closed to open and back to closed loop control provides a robust system that can operate with a minimum of supervision from medical personnel. Those qualities are essential in any system designed for residential or ambulatory use by sub-acute patients.

The following description illustrates some preferred methods for accomplishing these features, but it should be understood that in its essence the present invention provides for that movement from closed loop control to open loop control and back to closed loop control based on the presence of valid or invalid blood oxygen content measurements.

Figure 4:
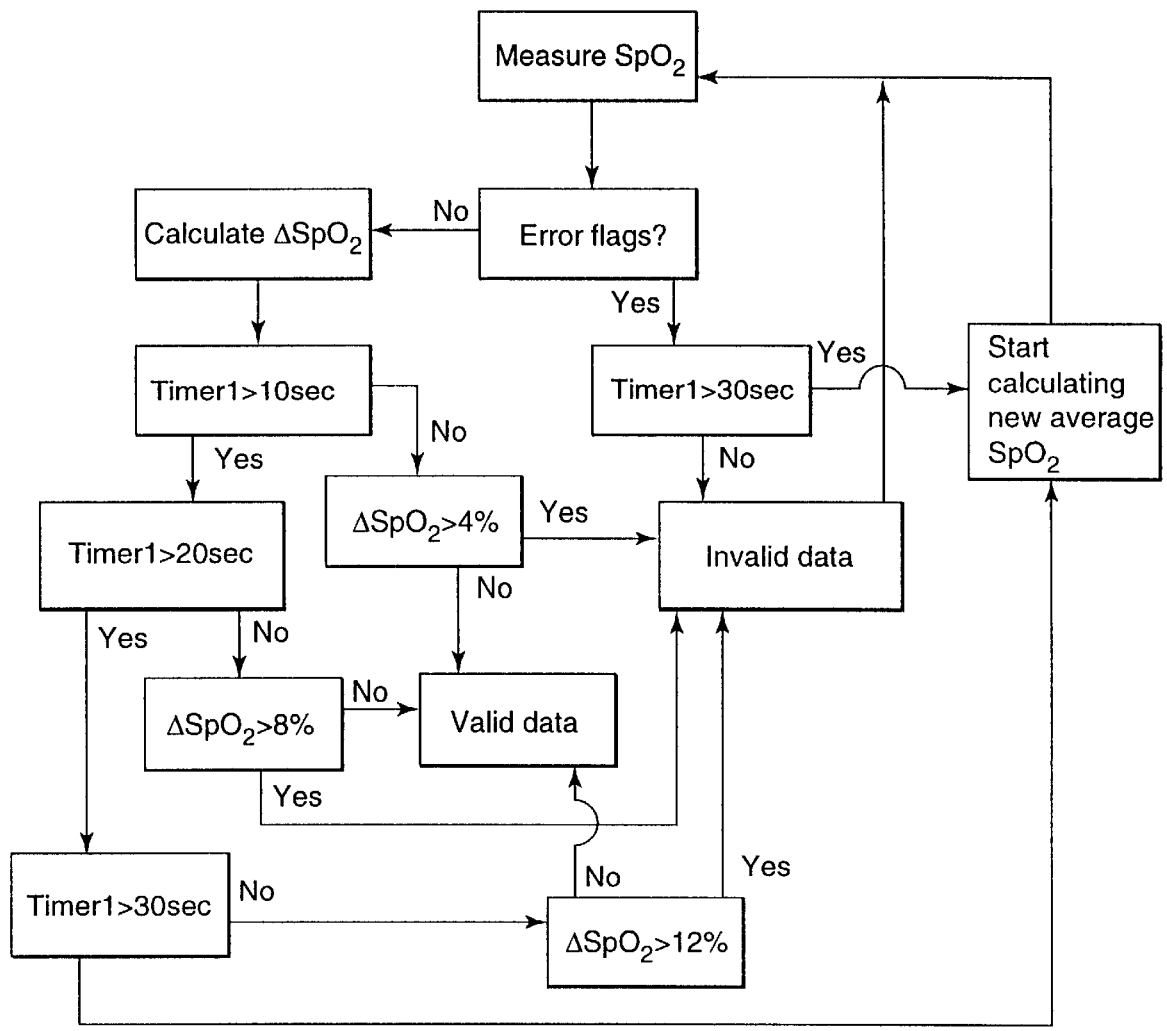
FIG. 4 is a flow diagram of one method of determining whether the measured blood oxygen content data is valid or invalid.

In one preferred embodiment, before the measured blood oxygen saturation reading ($SpO_2$) is used for determining the dose time D of oxygen to be delivered to the patient 16 from the oxygen source 20, various error handling and artifact detection procedures are followed to prevent erroneous over- or under-dosing of oxygen to the patient. In one preferred embodiment of the present invention, the error flags provided by the oxygen sensor 14 in the serial data stream are combined with a numerical analysis of the $SpO_2$ data to create an artifact detection and handling scheme (see FIG. 4 and the description below).

The serial data stream of the preferred pulse oximeter 14 gives three data points per second. Each point includes several bytes of information, as follows:

| | | |
|---|---|---|
| 1st byte = Status | Bit 7 | = Always set to "1" |
| | Bit 6 | = Sensor disconnected, set if true |
| | Bit 5 | = out of track, set if true |
| | Bit 4 | = low perfusion, set if true |
| | Bit 3 | = marginal perfusion, set if true |
| | Bit 2 | = bad pulse, set if true |

-continued

| | | |
|---|---|---|
| | Bit 1 | = heart rate bit 8 |
| | Bit 0 | heart rate bit 7 |
| 2nd byte = Heart Rate | (511 = bad data) Bit "7" is always set to "0" |
| | Heart Rate Data = Bits 0–6 |
| | Plus bits 0 & 1 of status byte to provide 9 bits of resolution |
| 3rd byte = $SpO_2$ | (127 = bad data) |

The first byte of the data stream has error flags for all of the major problems associated with pulse oximetry. These bits are examined for the occurrence of a disconnected sensor, poor or marginal perfusion, out of track oximeter and bad heart rate. If any of these flags is set the accompanying $SpO_2$ and heart rate data is ignored. If the data is determined to be invalid, a timer, Timer1, is started by the controller 10 which then waits for the next data point. The function of Timer1 is keep track of the length of time between valid pulse oximetry data points. Timer1 is reset to zero each time a valid data point is delivered.

If, however, none of the flags is set, in one preferred embodiment, a second error check is performed using a statistical analysis of the data. The new data point is compared to a mean value of previous data points which represents the patient's current blood oxygen content. The details of the calculation of this mean value are described below. The current data point is subtracted from the mean value to generate a difference, $\Delta SpO_2$ in %. (For the data-validity analysis below, if $\Delta SpO_2$ is less than zero, its absolute value is used.) If the absolute value of $\Delta SpO_2 > 4\%$ and Timer1 equals zero (i.e., the last data point was valid), then the current data point is determined to be invalid. Since the time between data points in the serial data stream will be about one-third of a second, a change larger than 4 percent in the $SpO_2$ in such a short time would be physiologically impossible. If the data point is determined to be invalid using this procedure, the data is ignored, Timer1 is started and controller 10 waits for the next data point.

If, however, the absolute value of $\Delta SpO_2 > 4\%$ and Timer1 does not equal zero, then additional evaluation is performed. The observed rate of oxygen desaturation in humans can approach 20%/minute or about 3% every 10 seconds. If Timer1 is less than 10 seconds and the absolute value of $\Delta SpO_2 > 4\%$, then the data is considered to be invalid. If Timer1 is greater than 10 seconds, but less than 20 seconds then the acceptance criteria is absolute value of $\Delta SpO_2$ less than 8% for the data to be valid. If Timer1 is greater than 20 seconds, but less than 30 seconds then the acceptance criteria is absolute value of $\Delta SPO_2$ less than 12%. If Timer1 is greater than 30 seconds, then oxygen is delivered using the default method which is described in detail below. It should, of course, be understood that, in the above analysis, the specific values of 4%, 8%, and 12%, and the specific times of 10, 20 and 30 seconds could be replaced with different values.

If the data point passes all the tests, Timer1 is set to zero and the new mean value of blood oxygen content is calculated with the most recent data point. The new mean value is then compared to the setpoint and a dose time D is calculated as detailed above in Equations 2–5.

In one preferred embodiment, an exponentially-weighted arithmetic mean of the previous data points is used to represent the current blood oxygen content. The new mean is calculated as follows:

$$\text{new mean} = (\text{current data point}) * W1 + (\text{previous mean}) * W2 \quad (6)$$

where $$W1 = 1 - \exp(-\Delta t/T) \qquad W2 = \exp(-\Delta t/T). \quad (7)$$

Here $\Delta t$ is the time between data points (0.33 seconds using the preferred oximeter), and T is a parameter which represents an appropriate time scale for the averaging. If an appropriate value of T is chosen, the exponentially-weighted mean will smooth out normal point-to-point "noise" fluctuations in the pulse oximeter data without masking the real trends related to the patient's blood oxygen content. (A typical value would be T=10 seconds, although other values could be used.)

Other methods could also be used to determine a mean value that is representative of the patient's current blood oxygen content. For example, a harmonic, or geometric mean might be used. (Descriptions of these types of means can be found in "Standard Mathematical Tables" by CRC Press, 24th edition, pages 470–471.) Alternately, a "running" mean might be used. In this method, the mean of a fixed, predetermined number of the most-recent data points could be used. For example, with the preferred pulse oximeter which delivers three data points per second, one could average the preceding 30 data points, thus calculating a mean which represents the patient's blood oxygen content for the previous 10 seconds.

It should be understood that other methods for recognizing and handling erroneous data from the oxygen sensor could be devised. Those skilled in the art could create different algorithms for handling invalid data, such as replacement of invalid data points with interpolated values based on the recent trend in the blood oxygen saturation. Alternative methods of identifying and rejecting invalid data should be considered to be within the scope of the present method and system.

In the preferred embodiment, the dose time D of oxygen that is delivered to the user depends on the validity (as described above) of the oxygen sensor data. In one preferred embodiment, if the time since the most-recent, valid data point, as indicated by Timer1, exceeds a predetermined, physiologically-relevant time scale for patient desaturation (referred to as Desattime), alternative, "default" oxygen delivery procedures are employed. In one embodiment Desattime is equal to 30 seconds. The default assumption is that a patient is always in need of oxygen, unless the blood oxygen content sensor positively indicates that they are not.

In the preferred embodiment, if the current oxygen sensor data is invalid, but Timer1 is less than Desattime, the oxygen dose time D will remain unchanged from its current value. The system controller 10 will continue to provide this same dose time to the sensor and valve controller 42. The sensor and valve controller 42 will provide a dose of this duration at the onset of inhalation. The process of gathering and evaluating blood oxygen saturation data then continues. Prior to the onset of invalid data, the system was either administering oxygen to correct a deficiency or the patient was in no need of oxygen. Thus, in this embodiment it is assumed that the patient's oxygen needs have not changed during this short time of invalid data and the status quo is maintained. If the patient was receiving no oxygen prior to the invalid data (i.e., dose time D=0), the valve controller 42 will not administer any oxygen. If, however, the patient was receiving oxygen (D>0), the valve controller 42 will continue to administer the same dose by responding to inhalation as described above. This will continue until either the data is valid once more and a reevaluation can be made of the patient's condition or Timer1 exceeds Desattime.

If the oxygen sensor data continues to be invalid and Timer1 exceeds Desattime, then the device will default to another oxygen delivery method. In the default method, the controller 10 will default to administering a prescription-equivalent dose of oxygen to the patient 16 from the oxygen source 20 via the demand delivery module 12. This default dose of oxygen could take many forms: In one embodiment, the default could be a continuous flow of oxygen. To implement this, the controller 10 would output a very large dose time to the sensor and valve controller 42. The sensor and valve controller 42 would thereby hold valve 26 in the position which allows oxygen to flow from source 20 to patient 16. Alternately, in the preferred embodiment, the default mode would provide a short dose of oxygen (of duration D=Ddefault) at the onset of inhalation for almost every breath. In this preferred embodiment, Ddefault would be shorter than a typical inhalation period, in which case the inhalation and valve controller 42 would provide pulses of duration Ddefault synchronized with each inhalation (demand mode). This will continue until such time as the blood oxygen content data is valid and closed loop control over oxygen delivery can start anew.

It is possible to envision additional alternate methods of default flow. In one such alternate embodiment, the valve does not necessarily open with each and every breath. It should be understood that these alternate methods of implementing a default flow still fall within the scope of the present invention. The object of the default method is to provide a total flow of oxygen during this period of default operation that is no less than the physiological equivalent amount that is prescribed to the patient by the physician. (Physiological equivalence meaning the amount dispensed by other demand delivery devices to provide adequate oxygen therapy.) It should be understood that the notion of physiological equivalence as regards demand delivery devices will change over time as their effects on the physiology of COPD patients is better understood by the medical community. Current practice indicates that 35 ml delivered every other breath at the beginning of inhalation is equivalent to a continuous flow of 2 liters/minute of pure oxygen.

In one preferred embodiment of the invention, the duration of the default dose (Ddefault) will be set by the patient's respiratory therapist using a hardware switch on the user interface 32. In the preferred embodiment, this switch is not accessible to the patient. The inventors appreciate the fact that other ways of setting the pulse width may be possible, such as a push button, etc.

Also, in the preferred embodiment, if Timer1 exceeds Desattime, then the previous mean value of the blood oxygen saturation is reset and data acquisition starts anew. In this way, it is assumed that the old $SpO_2$ information is no longer valid for the patient's current physical state and that to properly administer oxygen a more current measure of the blood oxygen level is needed. Thus, by using Timer1, a period of invalid data that exceeds Desattime will always lead to the administration of oxygen to the patient. This will correct any undetected desaturation events. Moreover, the controlling means 10 will always use the most current, valid information regarding the patient's blood oxygen level.

Those skilled in the art will understand that a wide range of possibilities for oxygen delivery in default mode beyond those that have been described here could be used. Although they are not described in detail herein, they should be considered as falling within the scope of the methods according to the present invention.

In one preferred embodiment, if invalid data is a problem, the controller 10 may be used to notify the patient of a problem with the pulse oximetry via the user interface 32 and/or alarm 38. This notification may take the form of a LED warning light, LCD readout, buzzer or some combination of these. Those skilled in the art may also conceive of other methods of warning the user that are not detailed herein. After the warnings have been issued and default demand flow mode entered, the controller 10 resumes monitoring the output of the oxygen sensor for valid data.

Along with monitoring the breathing cycle for oxygen delivery, the invention makes provision for the detection of apnea, the cessation of breathing for a prolonged period of time. Timer2 starts each time an inhalation is detected. If the elapsed time between breaths is greater than a predetermined time, e.g., 15 seconds, as determined by Timer2, then the inhalation sensor and valve controller 42 drives an alarm circuit 38 via controller 10 to signal the patient of a possible apneic event. These alarms stop sounding upon detection of the next inhalation.

Various methods and systems for conserving supplemental oxygen delivery to a sub-acute patient based on continuous blood oxygen content measurements and inhalation have been described above. Many changes, alterations and variations of the subject invention will become apparent to those skilled in the art after consideration of this specification and the accompanying figures and diagrams of the preferred embodiments. For example, the values chosen for, e.g., $\Delta SpO_2$, Timer1, Timer2, etc., are intended to be exemplary of some preferred values and should not limit the scope of the invention unless the values are explicitly recited in the claims. All such changes, modifications, variations, etc. are deemed to be covered by the claims which follow.

What is claimed is:

1. A method of controlling supplemental oxygen delivery during sub-acute care comprising:

continuously measuring blood oxygen content of a patient to obtain a measured blood oxygen content level;

delivering supplemental oxygen from an oxygen source to the patient when the patient is inhaling if the measured blood oxygen content level is below a desired value;

restricting the delivery of supplemental oxygen to the patient if the measured blood oxygen content level of the patient is above the desired value or when the patient is not inhaling;

determining if the measured blood oxygen content level is invalid; and delivering a default amount of supplemental oxygen to the patient when the patient is inhaling if the measured blood oxygen content level is invalid.

2. A method according to claim 1, wherein the supplemental oxygen is delivered through a nasal cannula.

3. A method according to claim 1, wherein restricting the delivery of supplemental oxygen comprises preventing the delivery of supplemental oxygen.

4. A method according to claim 1, further comprising determining when the patient is inhaling.

5. A method according to claim 4, further comprising sensing when the patient is inhaling using a flow sensor.

6. A method according to claim 1, wherein the method is performed in a residential setting.

7. A method of controlling supplemental oxygen delivery for sub-acute care comprising:

continuously measuring blood oxygen content of a patient to obtain a measured blood oxygen content level;

determining when the patient is inhaling;

delivering supplemental oxygen from an oxygen source to the patient through a supplemental oxygen delivery device when the patient is inhaling if the measured blood oxygen content level is below a desired value;

restricting the delivery of supplemental oxygen to the patient through the supplemental oxygen delivery device if the measured blood oxygen content level of the patient is above the desired value or when the patient is exhaling;

determining if the measured blood oxygen content level is invalid; and delivering a default amount of supplemental oxygen to the patient when the patient is inhaling if the measured blood oxygen content level is invalid.

8. A method of controlling supplemental oxygen delivery for sub-acute care comprising:

continuously measuring blood oxygen content of a patient to obtain a measured blood oxygen content level;

delivering a variable dose of supplemental oxygen from an oxygen source to the patient when the patient is inhaling, wherein the variable dose is at least partially determined based on the measured blood oxygen content level;

restricting the delivery of supplemental oxygen when the patient is not inhaling;

determining if the measured blood oxygen content level is invalid; and delivering a default amount of supplemental oxygen to the patient when the patient is inhaling if the measured blood oxygen content level is invalid.

9. A method according to claim 8, wherein the variable dose of supplemental oxygen is at least partially based on a trend in measured blood oxygen content as measured at different times.

* * * * *